United States Patent [19]

Miller

[11] Patent Number: 5,094,251
[45] Date of Patent: Mar. 10, 1992

[54] RELATING TO RESTRAINT ARRANGEMENTS

[75] Inventor: Paul G. Miller, Colne, England
[73] Assignee: Chester-Bowes Limited, Lancashire, England
[21] Appl. No.: 530,346
[22] Filed: May 30, 1990
[51] Int. Cl.⁵ .................. A61B 19/00; A61F 5/37
[52] U.S. Cl. ................................. 128/869; 128/872
[58] Field of Search ............ 128/869, 872, 873, 874, 128/875, 876, 846; 5/482, 486

[56] References Cited

U.S. PATENT DOCUMENTS

| | | | |
|---|---|---|---|
| 1,885,558 | 11/1932 | Smith | 128/872 |
| 2,062,611 | 12/1936 | Rosenthal | 128/872 |
| 2,151,434 | 3/1939 | Malah | 128/872 |
| 2,481,741 | 9/1949 | Graves | 128/873 |
| 2,567,082 | 9/1951 | Shuster | 128/872 |
| 2,722,694 | 11/1955 | Bryant | 128/872 |
| 2,948,278 | 8/1960 | Topa | 128/873 |
| 4,485,806 | 12/1984 | Akers | 128/873 |
| 4,524,768 | 6/1985 | Serrao | 128/873 |
| 4,653,131 | 3/1987 | Diehl | 128/872 |
| 4,679,267 | 7/1987 | Thiele | 128/872 |
| 4,858,625 | 8/1989 | Cramer | 128/872 |
| 4,860,771 | 8/1989 | Burgos | 128/872 |

Primary Examiner—Robert A. Hafer
Assistant Examiner—Michael Brown
Attorney, Agent, or Firm—Richard E. Jenkins

[57] ABSTRACT

A center portion extends loosely over a person on a mattress such that the person has freedom of movement on the central region of the mattress. The portion is secured by zips at either side to side portions which are secured to tubular members at either side. Movement of the person towards or over one side of the bed is limited by the center portion being placed in tension with the side portions preventing the person from moving towards or over or falling off the side of the bed.

1 Claim, 6 Drawing Sheets

RELATING TO RESTRAINT ARRANGEMENTS

The present invention relates to restraint arrangements and to a method of using restraint arrangements and to a method of restraining a person particularly, although not exclusively, related to the restraint of people lying in beds.

BACKGROUND ART

At present, in hospitals where it is required to ensure that a patient does not roll off a bed, cot sides are erected. The cot sides comprise an articulated frame located at each side of the bed which can either occupy a collapsed position or a raised position in which they project above the mattress of the bed and are abutted by a patient to prevent them from rolling off the bed.

The cot sides are expensive to manufacture and tend to remain permanently attached to each bed, regardless of whether they are required. Furthermore, when they are being moved between the collapsed and raised positions they tend to become entangled with the bedclothes and may trap an operators fingers. The cot sides are difficult to dismantle from the bed and are bulky and thus awkward to store. They also tend to trap dirt and germs and are difficult to clean. The cot sides are heavy, making operational movement or attachment or detachment to the beds a problem. A further disadvantage is that patients can climb over or around the cot sides in order to get out of the bed. The presence of the cot sides presents a clinical appearance to the bed which can be disarming to the patients.

In U.S. Pat. No. 4,074,375 (Kella) a restraint arrangement is provided to severely limit the degree of movement of a patient in a bed. A blanket is provided with longitudinal, transverse and diagonal straps to act as a restraining means and the purpose of all those straps must be to inhibit as much movement as possible of a patient in the bed. Certainly there is no disclosure of a cover according to one aspect of the present invention which is specifically designed to allow a person (not necessarily a patient) maximum freedom of movement on the mattress Furthermore, there is no way in which a patient in a bed having a cover according to Kella could ever reach the edge region of a bed against the restraint provided by the straps. Also, in Kella, the restraint can only be divided into two portions thus necessitating the complete detachment of the restraint from the bed before the restraint can be replaced.

A number of other prior proposals exist for restraining movement of an occupant in a bed which cannot be easily replaced without undoing the attachment of the covers from the bed.

In U.S. Pat. No. 4,653,131 (Diehl) the fabric restraint (even without the reinforcing straps of Kella) holds a patient in a surpine position. In European Patent Publication No. 165 043 A3 (Brooks) a restraint cover holds a child in a flat position with the child being located between upper and lower layers which are comprised by a continuous portion which is folded.

U.S. Pat. No. 3,857,124 (Hadley) discloses a bottom sheet which is secured to a mattress with a bedspread being releasably secured to the bottom sheet. However the purpose of the bedspread being so attached is to ensure that the bed cover remains in place and if the patient were to move over the side of the mattress then the mattress would roll of the bed or the bottom sheet would be pulled round the mattress thus allowing the patient to fall to the ground.

DISCLOSURE OF INVENTION

According to one aspect of the present invention, a support and restraint arrangement comprises a supporting surface arranged to support a person reclining on that surface and a restraint cover arranged, in use, to extend over a person located on the supporting surface, the restraint cover in the region of each side of the supporting surface being prevented from moving substantially towards the opposite side of the supporting surface.

The restraint cover may be secured or anchored in position in the region of each side of the supporting surface and the securing or anchoring may extend along substantially the complete length of at least one side of the restraint cover or supporting surface.

The support cover may be secured in position in the region of the sides of the supporting surface by attachment means provided on the cover. The attachment means may comprise straps. The attachment means may be releasable to enable the support cover to be removed. The attachment means may co-operate with a frame. The supporting surface may be provided by a mattress, and the mattress may rest on the frame with which the attachment means co-operate. Alternatively, the support cover at the region of the sides of the supporting surface may be prevented from moving substantially towards the opposite side by being trapped between an upper and lower layer, in which case the support cover may extend between the sides of the supporting surface beneath that surface.

The restraint cover may include two portions which can be separated from each other along at least part of their length. The portions may be separable from each other along their complete length. The portions may be separated from each other in a direction extending transverse to the direction between the sides. The portions may be separated from each other in a region spaced from the sides of the supporting surface or in the region of at least one side of the supporting surface. A plurality of portions may be provided which can be interchanged and those portions may be of different configuration.

According to another aspect of the present invention, a restraint cover is adapted to extend over a supporting surface and, in the region of each side of the supporting surface, is arranged to be prevented from moving substantially towards the opposite side of the supporting surface.

According to another aspect of the present invention a restraint arrangement includes a restraint arranged to extend from a first side of a supporting surface to a second side of a supporting surface, the restraint being arranged to extend over a person located on the supporting surface characterised in that the restraint is arranged to extend from a first side of a supporting surface to a second side of a supporting surface, the restraint being arranged to extend over a person located on the supporting surface characterised in that the restraint is arranged to extend over a person located on the supporting surface when the person is located centrally thereon to permit freedom of movement of that person with the person being arranged to co-operate with the restraint to limit the extent of movement of that person towards or over the second side of the supporting surface with the restraint being retained whereby significant movement of the restraint away from the first side towards the second side is prevented.

According to another aspect of the present invention a method of restraining a person located on a supporting surface with a restraint extending from a first side of the supporting surface over the person to a second side of the supporting surface is characterised in that the person has freedom of movement when located centrally on the supporting surface but co-operates with the restraint to limit the extent of movement of the person towards or over the second side of the supporting surface by the restraint being retained by significant movement of the restraint away from the first side towards the second side being prevented.

According to another aspect of the present invention a restraint arrangement includes a restraint arranged to extend from a first side to a second side of a supporting surface, the restraint including an upper portion arranged to extend over a person located on the supporting surface characterised in that the restraint is arranged to extend over a person located on the supporting surface with the person being arranged to co-operate with the restraint to limit the extent of movement of that person towards or over the second side of the supporting surface, the restraint being arranged to be connected at either side to a fixed portion, the restraint being retained whereby significant movement of the restraint away from the first side towards the second side is prevented with the upper portion being arranged to be detachable without detaching the restraint from its connection at either side to the fixed portion.

According to a further aspect of the present invention a method of using a restraint arrangement in which a restraint extends from a first side of a supporting surface over the person to a second side of the supporting surface and is secured to a fixed portion at either side is characterised in that the person co-operates with the restraint to limit the extent of movement of the person towards or over the second side of the supporting surface by the restraint being retained by significant movement of the restraint away from the first side towards the second side being prevented and an upper portion of the restraint is detachable without disconnection of the restraint at either side of the fixed portion.

BRIEF DESCRIPTION OF DRAWINGS

The present invention may be carried into practice in various ways, but several embodiments will now be described by way of example and with reference to the accompanying drawings, in which.

DETAILED DESCRIPTION OF DRAWINGS

Figure 1:
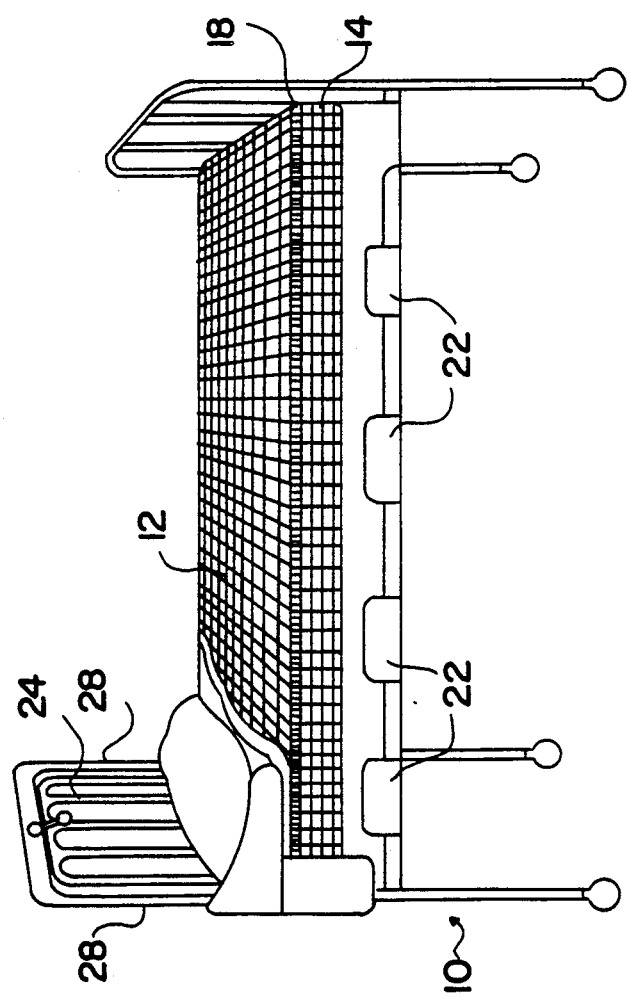
FIG. 1 is a perspective view of a metal framed bed including a first embodiment of a restraint cover.
Figure 2:
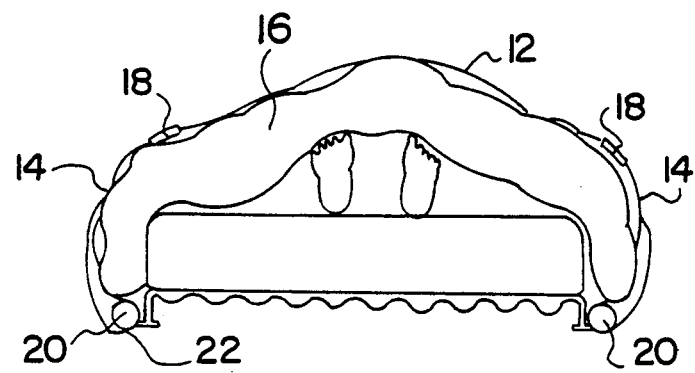
FIG. 2 is a cross-section through the lower region of the bed shown in FIG. 1 with an occupant in the bed.

As shown in FIGS. 1 and 2 a metal framed bed 10 has a restraint covering provided comprising a centre portion 12 and two side portions 14.

In use, as shown in FIG. 2, the centre portion 12 extends over the conventional bedding 16 and is connected by zips 18 to an upwardly extending edge of each side portion 14. Each side portion 14 is connected to a longitudinal tubular member 20 of the bed running down either side of the bed by straps 22 which surround the tubular members. If desired, a valance may be secured to the side portions 14 such that the valance hangs down and conceals the sides of the bed and the straps 22 with the valance normally remaining in place when changing the centre portion.

Should the person tend to roll towards one side of the bed then the movement is limited by the centre portion being placed in tension or being placed in further tension, with that tension being resisted by the co-operation of the straps 22 with the tubular member 20 at the other side of the bed. The person may either be constrained to be able to be adjacent to the edge of the bed or, if desired, it may be that the person could come to rest just over the edge of, and slightly down the side of the bed in which case they become suspended by the restraint cover.

The restraint cover is secured to the head frame 24 of the bed by straps 26 which extend around the side tubular members 28 of the head frame. The straps 26 prevent the cover from moving down the bed and off an occupant of the bed thereby allowing them to roll off.

Figure 3:
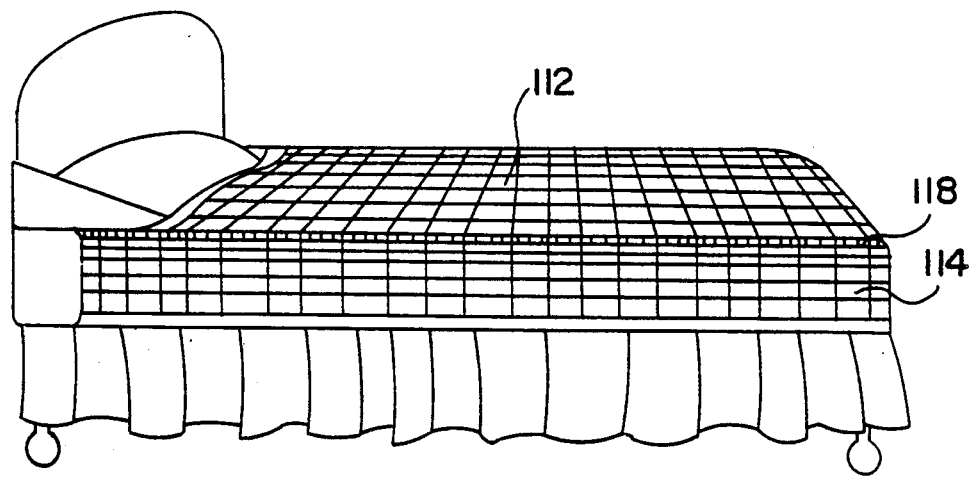
FIG. 3 is a perspective view of a divan bed including a second embodiment of a restraint cover.
Figure 5:
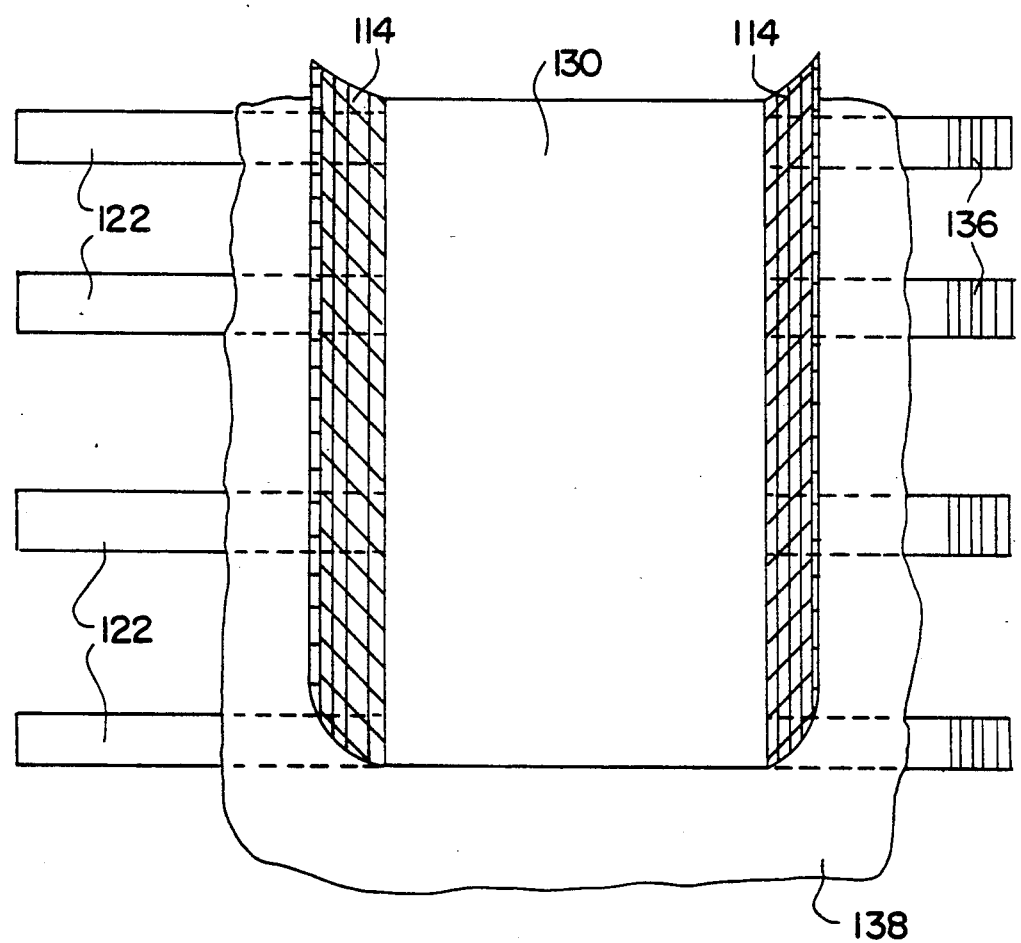
FIG. 5 is a plan view of the restraint cover shown in FIGS. 3 and 4 with the cover laid out flat and and a central portion of the cover missing.
Figure 4:
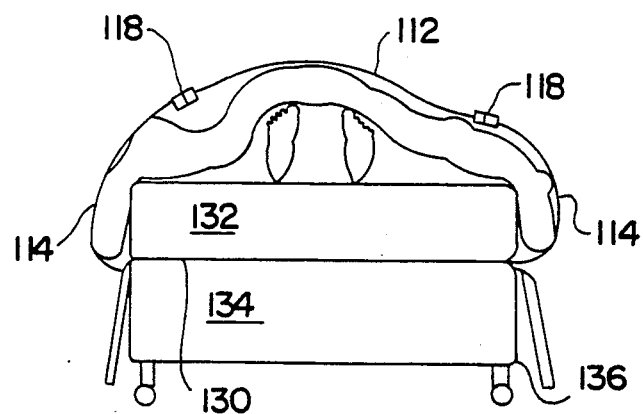
FIG. 4 is a view similar to FIG. 2 of the bed shown in FIG. 3.

FIGS. 3 and 4 illustrate the attachment of a restraint cover to a conventional divan bed. Similar parts to those in FIGS. 1 and 2 have been given the same reference numeral prefixed by the number 1. The cover includes a centre portion 112 which is secured at either edge to side portions 114 by respective zips 118. The side portions are connected to each other by a sheet 130, shown in FIGS. 4 and 5, which extends beneath the mattress 132 and above a base frame 134. The mattress 132 traps the sheet 130 in place, but additional security is provided by a series of four straps 122 which are secured to one side of the sheet 130 and which pass under the base frame 134 and are secured to shorter straps 136 extending from the other side of the sheet 130.

A valance 138 extends from either side and one end of the sheet 130 to cover the straps 122 and 136 whereby the bed presents a conventional appearance, at least from beneath the mattress.

Figure 6:
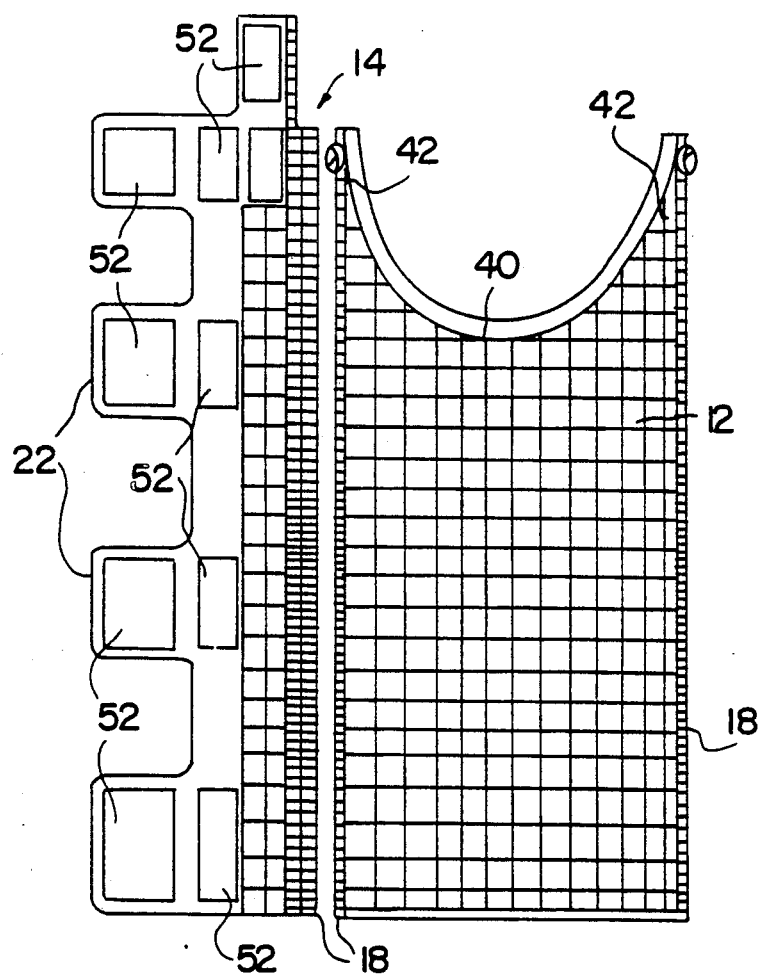
FIG. 6 is a plan view of a centre portion and a side portion of an alternative cover.
Figure 7:
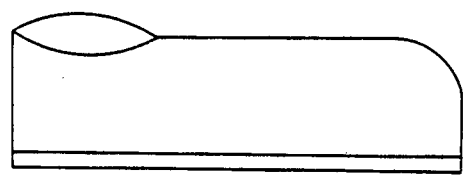
FIG. 7 is a schematic side view of a person located within the cover shown in FIG. 6.

FIG. 6 illustrates the shape of the centre portion 12 shown in FIGS. 1 and 3. One end of the centre portion 12 includes an arcuate recess 40 which allows the head of the occupant to be exposed with restraint against movement of the head off or towards one side of the bed being resisted by the sides 44 defining the recess, as shown in FIG. 7.

Figure 9:
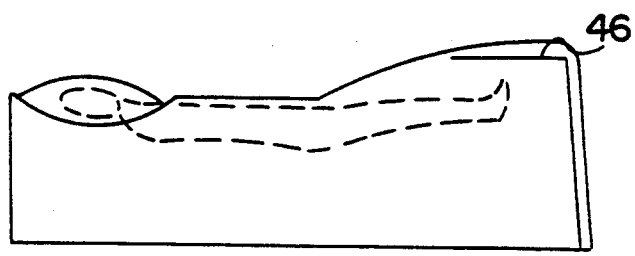
FIG. 9 is a schematic sectional view through an occupied bed including a centre portion as shown in FIG. 8.
Figure 8:
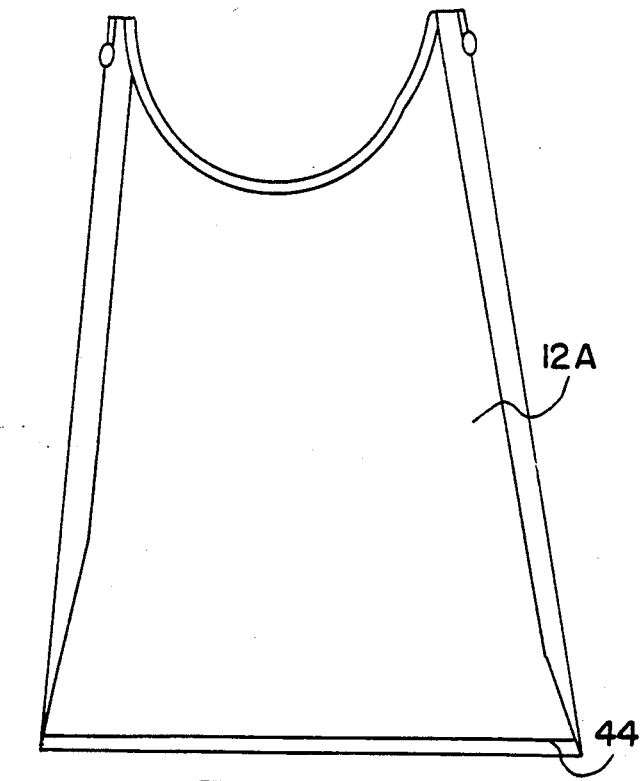
FIG. 8 is a plan view of a further embodiment of a centre portion.

In FIG. 6 the width of the centre portion 12 is constant throughout its length. FIG. 8 illustrates an alternative centre portion 12A which can be fitted to either of the side portions shown in FIGS. 1 and 3. The width of the centre portion 12A increases towards the foot region 44 in order that there may be adequate room for a foot cradle 46, as shown in FIG. 9.

Figure 10:
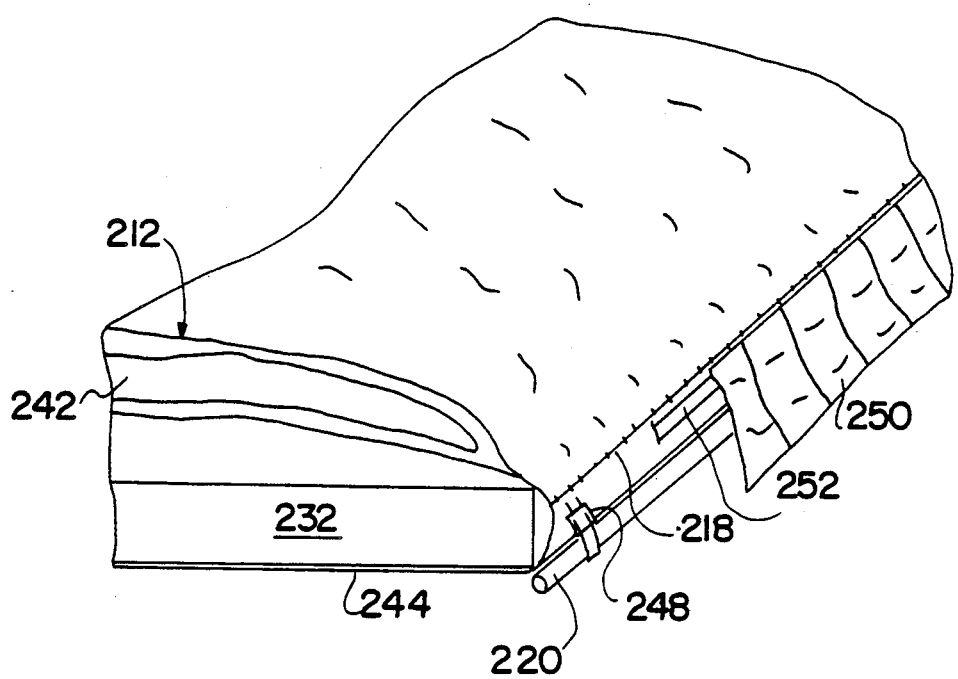
FIG. 10 is a schematic perspective view of part of the side of a hospital bed.

FIG. 10 illustrates a quick release cocoon in which the centre portion 212 comprises a duvet cover with a duvet 242 located in that cover. The sides of the cover are secured to a bottom sheet 244 at either side by zips 218 (only one of which is shown). The sheet 244 is connected at either side to the side tubes 220 by four quick release fasteners 248 spaced along each side. The fasteners 248 can be pushed to connect them or squeezed to release them. The fasteners 248 are either directly tied to the tubes 220 or connected across the underside of the mattress 232. A valance 250 can be secured to a velcro 252 strip along each side of the sheet 244 such that the valance obscures the tubes 220.

Figure 11:
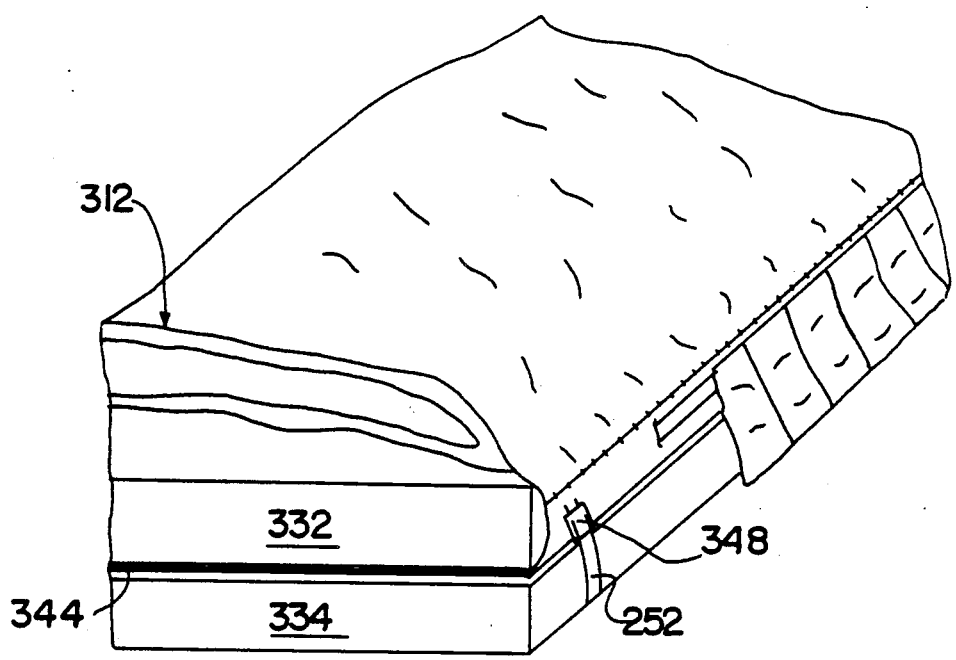
FIG. 11 is a view similar to FIG. 10 of a divan bed.

In FIG. 11 a similar centre portion 312 and bottom sheet 344 are provided to those shown in FIG. 10 on a divan bed, with the quick release fasteners 348 being provided at the upper outer ends of four straps 252 which extend under or surround the base 334 of the divan bed.

In either of the embodiments described in FIGS. 10 or 11 the fasteners 248 or 348 can be released and the mattress, duvet and bottom sheet moved off the bed in order to move the occupant to a safe place, for instance in the event of a fire. A person thus moved is retained in safety and relative comfort by the cocoon. Four handles can be provided, possibly at the corners of the mattress in order to manoeuvre the patient in this way.

It is envisaged that the cocoon effect provided by the illustrated restraint cover will be afforded by a nylon net which will ordinarily rest on the bed clothes. However, it may be desirable to have the cover in tension during normal use. The cover may be elastic or nonelastic. The restraint cover may be washable. The restraint cover, and in particular the centre portion may comprise a quilt cover in which case the restraint not only serves to prevent an occupant from falling off the bed but also serves to keep the cover in position over the mattress. When the centre portion comprises a quilt cover, the cover need not necessarily be attached at the sides and could act as a conventional quilt. Furthermore, the restraint cover may be detachable from the side portions to allow replacement by a clean or different centre portion without the side portions necessarily being detached from the bed.

The zip or zips of any of the described restraint covers may be operable by an occupant of the bed.

The illustrated cover given an occupant freedom of movement such that they can sit up, roll over, or lie in any position but are prevented from rolling or moving towards an edge or are held when they move over the edge.

The illustrated bed may be 0.91 m wide and the mattress may be 0.13 m deep. The duvet cover may be 1.47 m wide and the net cover may be 1.45 m wide. Accordingly the cover may be between 10 and 15 per cent wider than the distance which it has to extend across, and may be in the region of 12.4. per cent wider.

Although the invention has been described with specific reference to beds, it will be appreciated that ambulance beds, stretchers and trolleys could be provided with restraint covers which are described.

What I claim is:

1. A bed restraint for use with a mattress and a mattress support surface thereunder comprising:
   a lower portion adapted to extend over and to be secured to a support surface beneath the mattress of a bed, and defining opposing longitudinally extending first and second sides wherein each side includes a first mating portion of a zipper positioned along at least a portion of the length thereof so as to be adjacent the top edge of the support surface; and
   a detachable upper portion adapted to overlay and overlap the sides of the mattress and defining longitudinally extending first and second sides wherein each side includes a second mating portion of a zipper positioned along at least a portion of the edge thereof so as to releasably engage the corresponding first mating portion of a zipper on a respective side of said lower portion adjacent the bottom edge of the mattress;
whereby said detachable upper portion serves to extend over a person located on said support surface so as to limit the extent of movement of said person towards or over said first or second side of said support surface but to allow the person to roll over said support surface and the lower portion of said restraint when positioned centrally thereon.

* * * * *